United States Patent [19]

Kowal et al.

[11] Patent Number: 5,770,630
[45] Date of Patent: Jun. 23, 1998

[54] MANUFACTURE OF ORGANIC LIQUIDS

[75] Inventors: Wieslaw Mark Kowal, Sunnyview; Geoffrey Frederick Skinner, Kimblewick, both of United Kingdom

[73] Assignee: Foster Wheeler Energy Limited, Reading, England

[21] Appl. No.: 383,694

[22] Filed: Feb. 1, 1995

Related U.S. Application Data

[63] Continuation of Ser. No. 988,882, Dec. 10, 1992, abandoned, which is a continuation-in-part of Ser. No. 711,258, Jun. 4, 1991, abandoned, which is a continuation of Ser. No. 466,987, Jan. 18, 1990, abandoned, which is a continuation of Ser. No. 132,685, Dec. 14, 1987, abandoned, which is a continuation-in-part of Ser. No. 910,640, Sep. 23, 1986, abandoned.

[51] Int. Cl.$^6$ ............................. C07C 27/06; C07C 31/04
[52] U.S. Cl. ........................... 518/706; 518/703; 518/705; 518/707; 518/713
[58] Field of Search .................................. 518/703, 705, 518/706, 707, 713

[56] References Cited

U.S. PATENT DOCUMENTS

| | | | |
|---|---|---|---|
| 2,276,274 | 3/1942 | Keith | 518/706 |
| 2,686,819 | 8/1954 | Johnson | 585/310 |
| 3,920,717 | 11/1975 | Marion | 518/703 |
| 3,940,428 | 2/1976 | Connell et al. | 518/705 |
| 4,064,156 | 12/1977 | McRobbie | 518/706 |
| 4,134,907 | 1/1979 | Stephens, Jr. | 518/721 |
| 4,346,179 | 8/1982 | Sugier et al. | 518/706 |
| 4,367,206 | 1/1983 | Pinto | 518/704 |
| 4,383,837 | 5/1983 | Smith | 48/197 R |
| 4,413,153 | 11/1983 | Garwood et al. | 585/304 |
| 4,455,394 | 6/1984 | Pinto | 518/705 |
| 4,549,396 | 10/1985 | Garwood et al. | 518/703 |
| 4,628,066 | 12/1986 | Bonnell et al. | 518/700 |

FOREIGN PATENT DOCUMENTS

| | | | |
|---|---|---|---|
| 267771 | 3/1988 | European Pat. Off. | 578/703 |
| 1046822 | 12/1953 | France . | |
| 1259945 | 1/1972 | United Kingdom | 518/706 |
| 2 047 249 | 11/1980 | United Kingdom . | |

OTHER PUBLICATIONS

"Methanol's Advantages, Disadvantages Cited," Oil & Gas Journal Jul. 14, 1986.

*Primary Examiner*—Richard L. Raymond
*Attorney, Agent, or Firm*—Finnegan, Henderson, Farabow, Garrett & Dunner, L.L.P.

[57] ABSTRACT

An improved process for the manufacture of organic liquids from gases containing hydrogen and carbon monoxide which avoids the build-up of nitrogen content through the use of a se ies of organic liquid reactors.

13 Claims, 4 Drawing Sheets

MANUFACTURE OF ORGANIC LIQUIDS

This application is a continuation of application Ser. No. 07/988,882 filed Dec. 10, 1992 now abandoned, which is a continuation-in-part of application Ser. No. 07/711,258 filed Jun. 4, 1991, now abandoned, which is a continuation of Ser. No. 07/466,987 filed Jan. 18, 1990, now abandoned, which is a continuation of Ser. No. 07/132,685 filed Dec. 14, 1987, now abandoned, which is a continuation-in-part of Ser. No. 08/910,640 filed Sep. 23, 1986, now abandoned.

This invention relates to the manufacture of organic liquids, by which it is meant compounds which (1) are liquids at atmospheric pressure and temperature and (2) are composed of carbon, hydrogen new paragraph.

In particular this invention relates to the manufacture of organic liquids from gases containing hydrogen, nitrogen, and carbon monoxide.

More particularly, the invention relates to processes in which the synthesis gas is manufactured by reactio of a hydrocarbon or other carbonaceous feed material with air or oxygen-enriched air, such that the synthesis gas contains a significant proportion of nitrogen.

Methods of producing organic liquids from mixtures of hydrogen and carbon monoxide (commonly called synthesis gas) are well known in the art. Methanol, for instance, is normally manufactured by reacting carbon oxides (mainly carbon monoxide) with hydrogen over a copper containing catalyst, whereby the locarbon oxides and hydrogen are converted to methanol.

Another well-known process that uses synthesis gas is the the Fischer Tropsch system, which is used to manufacture synthetic transportation fuels (gasoline and diesel).

Higher alcohols and olefins are among other products that may be manufactured from synthesis gas.

To achieve a more complete conversion of the synthesis gas into products, the effluent gas from the organic synthesis reactor is usually recycled to the reactor inlet, thus forming the well-known 'synthesis loop'. If the synthesis gas used in such a loop process is made by the partial combustion of a hydrocarbon or other carbonaceous material with air, the nitrogen present in the air will build-up to undersirable levels in the synthesis loop.

In order to synthesize organic liquids without an undesirable build-up of nitrogen in the synthesis loop, the nitrogen has to either be removed from the synthesis gas or the partial combustion process has to be accomplished in the absence of air, i.e., with oxygen.

The concept and practice of synthesizing hydrocarbon materials, particularly gasoline and diesel fuel, from hydrogen and carbon monoxide is well known. Typically, but not exclusively, the reaction proceeds according to the expression:

this requiring a synthesis gas having an $H_2/CO$ molar ratio of approximately 2.

Products containing carbon, hydrogen and oxygen, for example methanol or higher alcohols, may also be synthesized from hydrogen and carbon monoxide, typically according to the expression Synthesis gases for the above-mentioned processes may be produced by reaction of a feedstock such as natural gas, heavy oil or coal with an oxygen-containing gas.

The use of oxygen-enriched air or air alone as the oxidant gas reduces or eliminates the cost of an air separation (oxygen) plant. Moreover a significant proportion of nitrogen in the synthesis gas confers an unexpected advantage by reducing the concentration of water vapor in the outlet from the synthesis reactors, which can otherwise approach 90% as is illustrated by the conversion of, for example, inerts-free synthesis gas to octane:

The high water vapor concentration can cause undesirable incipient condensation of water, particularly with slurry type synthesis reactors.

With such a once-through arrangement, it is typically difficult to achieve an overall conversion of ($H_2$+CO) into the desired product(s) in excess of 90% or so. Consequently the tail-gas from the once-through process has a significant content of combustible gases. These gases consist of unconverted ($H_2$+CO) plus light hydrocarbon gases both originating in the synthesis gas production system and formed as by-products of the synthesis itself.

In order to dispose of the combustible content of the nitrogen-rich tail gas in an economical and environmentally acceptable way, it has been proposed to burn in it a boiler or a gas turbine by Garwood et al. (U.S. Pat. No. 4,549,396) or in a gas turbine integrated with the compression plant supplying the oxidizing gas to the process.

The combustion of the tail gas in a boiler or turbine is within the scope of the invention but it depends on there existing in the locality a demand for steam or electric power, since generally the total combustible heat content of the tail gas substantially exceeds the heat and power requirements of the synthetic fuels plant itself.

One objective of the present invention therefore is to provide a means of recycling most of the combustible content of the nitrogen-rich tail gas within the synthesis plant itself, thereby avoiding dependence on an external demand for heat/power.

SUMMARY OF THE INVENTION

The present invention provides a means for synthesizing organic liquids, such as methanol, from gases derived from the partial combustion of hydrocarbons or other carbonaceous materials with air. The present invention also provides a method for manufacturing organic liquids, such as methanol, without the undesirable build-up of nitrogen occurring within the system.

Accordingly, the present invention provides a process for manufacturing organic liquids from gases containing hydrogen, nitrogen and carbon monoxide comprising passing the gases through a series of two or more organic liquid synthesis reactors and condensing and removing organic liquid from the effluent stream from each of the reactors.

The present invention also provides a process for manufacturing organic liquids from gases derived from the partial combustion of hydrocarbons and other carbonaceous materials with air comprising passing the gases through a series of two or more organic liquid synthesis reactors and condensing and removing organic liquid from each of the reactors.

Since the recycle of unconverted ($H_2$+CO) from the outlet of the synthesis reactor(s) to a point upstream is impracticable with nitrogen-rich oxidants due to the resulting accumulation of nitrogen in the recycle loop, in order to achieve an acceptable conversion of ($H_2$+CO) into the desired product when these nitrogen-rich oxidants are used, a series of once-through reactors with intermediate removal of product is employed according to the present invention.

The invention also provides for the conversion of the carbon monoxide and some of the carbon dioxide in the tail gas into methane by reaction with the hydrogen present ("methanation"), then separation of the methanated gas into a methane-rich stream, which is recycled to the synthesis gas production section, and an almost combustible-free nitrogen waste stream. The waste nitrogen may be heated prior to expansion to atmospheric pressure through a turbine.

By this arrangement, all the combustible material in the tail gas from the synthesis unit, comprising not only the unconverted. hydrogen and carbon monoxide but also residual methane from the synthesis gas production and hydrocarbon gases formed in the syn,thesis section itself, can be recovered with only a small loss of energy.

In practice the physical separator, e.g., for separating methane, is a cryogenic separator, so it will be necessary to remove sufficient carbon dioxide upstream of the methanator to en-sure that the methanated gas is essentially free of carbon diox-ide. If carbon dioxide is needed in order to recycle some carbon dioxide to the synthesis gas production section, the cost increment in providing a carbon dioxide removal plant necessary for practice of the invention would be small.

DESCRIPTION OF THE PREFERRED EMBODIMENT

Accordingly, the inventionrelates to a process for manufacturing organic liquids wherein the liquids are alcohols, olefins and Fischer Tropsh products comprising:

(a) forming a gas comprising hydrogen, nitrogen and carbon monoxide by the partial oxidation of a hydrocarbon or other carbonaceous material with air;

(b) passing the gas without the removal of the nitrogen through two or more organic liquid synthesis reactors arranged in series, where the organic liquid synthesis reactors operate at a temperature rranging from about 200° F. to about 500° F. and a pressure ranging from atmospheric pressure to about 100 atmopsheres in the presence of a catalyst suitable for converting the gas to the organic liquid to form the organic liquid; and (c) condensing and removing the organic liquid from each of the reactors, where the condensation process takes place at a temperature ranging from −200° F. to about 300° F. and a pressure ranging from atmospheric pressure to about 100 atmospheres.

The proposed invention can be used for the manufacture of organic liquids such as methanol, ethanol and higher alcohols, Fischer Tropsch products and olefins.

The synthesis gases can be produced by a partial combustion of hydrocarbons, such as natural gas or petroleum, or other carbonaceous material, such as coal or coke, with air. Steam can also be present during the combustion process.

Any process can be used for partial combustion. An example of a process for the partial combustion of hydrocarbons is the Texaco partial oxidation process which operates at around 2500° F. and between 10 and 100 atmospheres. An example of a process for the partial combustion (i.e. gasification) of coal is the U-gas fluid bed process, which operates at around 1800° F. and at 5–15 atmospheres.

Whichever process is used for the partial combustion operation, the synthesis gas produced will have as its main constituents hydrogen, carbon monoxide and nitrogen.

For the efficient operation of the organic synthesis, it may be necessary for the synthesis gas to be essentially free of sulfur compounds, carbon dioxide and/or water vapor.

Sulfur compounds, if present in the feedstock, can be removed either from the feedstock before partial combustion or afterwards. In the case of a hydrocarbon gas feedstock containing a few parts per million of sulfur compounds, this would be best accomplished upstream of the partial combustion using an absorbent such as zinc oxide operating at around 700° F. In the case of a hydrocarbon gas with a large sulfur content (over 500 vpm), or a coal, coke, or petroleum oil, the removal of sulfur is best accomplished by washing the partial combustion product gas with a solvent, such as monoethanolamine solution at 100° F.

Carbon dioxide can be removed from the partial combustion product gas by a similar monoethanolamine process or other established washing process. Water vapor can be removed from the partial combustion product gas by cooling and condensation.

The resulting purified gas stream comprising mainly hydrogen, carbon monoxide and nitrogen is passed through a series of one or more reactors wherein the organic synthesis desired is performed.

Any number of synthesis reactors can be used within the scope of this invention. The number of reactors used in the organic liquid synthesis generally ranges from two to about four, depending on the liquid produced.

Any catalyst known in the prior art for synthesizing organic liquids can be used in this invention. Typical catalysts include copper and zinc-containing catalysts for methanol manufacture and iron oxide-based catalysts for Fischer Tropsch processing.

The organic liquid synthesis reactors generally operate at temperatures and pressures suitable to the catalyst being used. Typically, the synthesis reactor will operate at temperatures ranging from about 200° F. to about 500° F. and pressures ranging from about atmospheric to about 100 atmospheres.

The organic product is removed from the effluent stream from each reactor. This separation is generally carried out by cooling and condensing the organic product from the effluent. The condensation process takes place at a temperature ranging from about −200° F. to about 300° F. and a pressure ranging from atmospheric pressure to about 100 atmospheres.

Cooling and condensing can be supplemented or replaced, if desirable, by another separation process, such as washing with a suitable liquid or adsorption on a solid such as with molecular sieves.

The reactor effluent gas, after product separation, is then passed to the next reactor inlet.

The gas leaving the product separator following the final reactor is a waste gas stream that can be expanded to low pressure for use as a fuel. Optionally the waste gas stream can be processed to recover its hydrogen and carbon monoxide content for recycle to a point upstream.

Examples of such recovery include:

(1) Adding steam to the waste gas stream, passing it over a CO shift catalyst such as iron oxide so that the steam oxidizes most of the carbon monoxide to carbon dioxide with release of an equal volume of additional hydrogen, washing out the carbon dioxide present with a solvent such as monoethanolamine, and finally condensing out most of the nitrogen content of the gas to leave a gas stream consisting mainly of hydrogen. This may then be recycled to the synthesis operation.

(2) Passing the waste gas through an adsorbent such as molecular sieve so as to substantially separate its hydrogen content so that the hydrogen may be recycled to the synthesis operation.

(3) Washing carbon monoxide from the waste gas using a solvent such as 'Cosorb' such that the carbon monoxide removed may be recycled to the synthesis operation.

Figure 1:
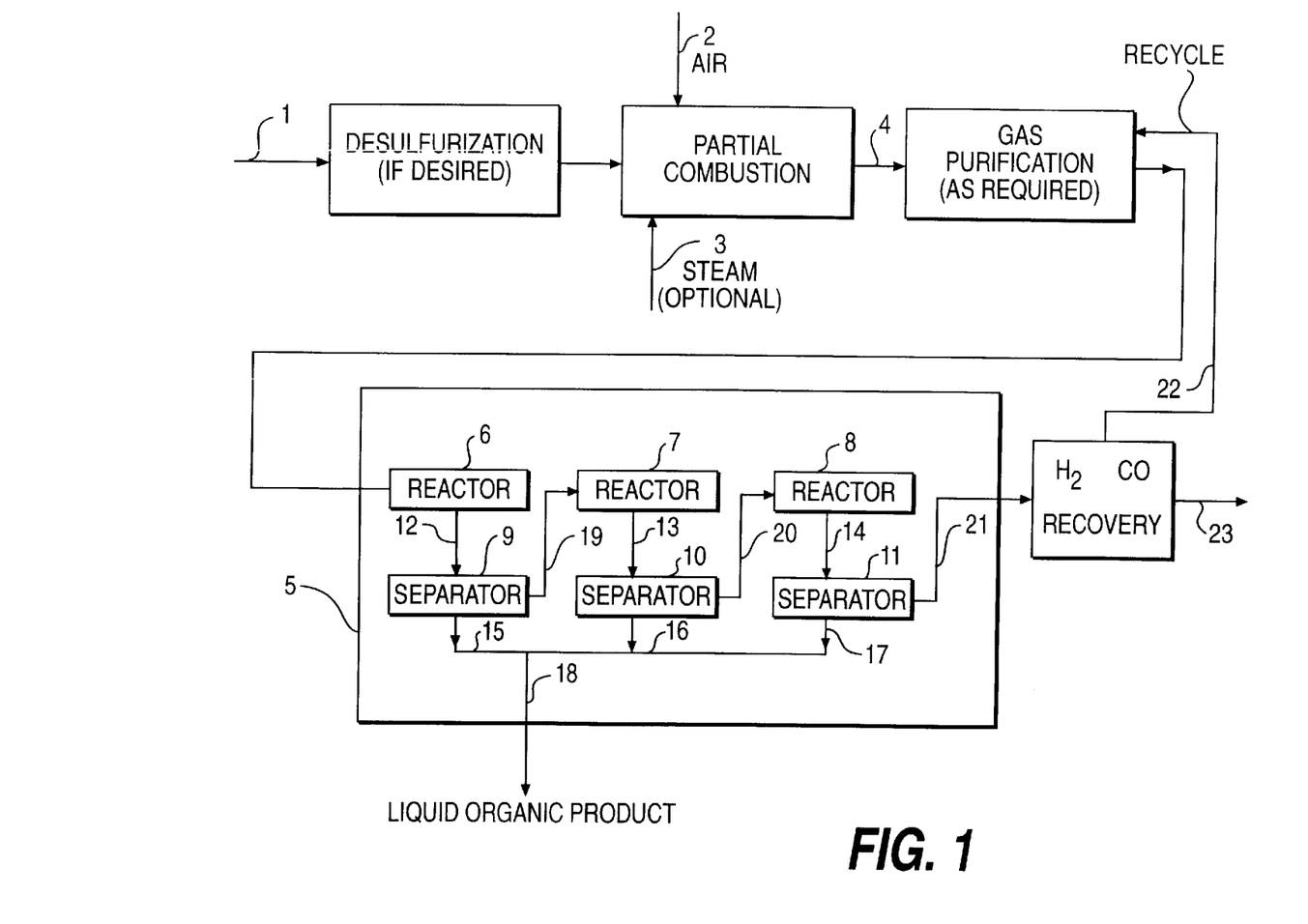
FIG. 1 is a flow diagram of an preferred embodiment of the present invention.

Referring to FIG. 1, in a preferred embodiment of this invention, hydrocarbons or other carbonaceous materials are fed via line 1 to an optional desulfurization step and then to a partial combustion step, where the hydrocarbons or other carbonaceous materials are combined with air via line 2 and optionally steam line 3 to partially combust the hydrocarbons or other carbonaceous materials to form a synthesis gas.

The synthesis gas then leaves the partial combustion step via line 4 where it can be subject to an optional purification step and then passed to an organic liquid synthesis zone 5. In the organic liquid synthesis zone, the synthesis gas is subjected to a series of reactors, 6, 7 and 8 which converts the synthesis gas to the desired fluid product. After passing through each reactor, the unreacted synthesis gas and organic liquid are fed to separators 9, 10 and 11 via lines 12, 13 and 14 for separation of the organic liquid from the unreacted synthesis gas. The organic liquid is then recovered via lines 15, 16, 17 and 18. The unreacted synthesis gas is passed to the next reactor via line 19 and 20. After a final separation step, a waste gas is recovered via line 21. The waste gas can be treated to recover $H_2$ and CO and recycled via line 22 or can be passed via line 23 for further use, such as a fuel.

EXAMPLE

The following text describes a typical application of the subject process, namely the manufacture of 585 short tons/day of cetane (hexadecane) and 1190 short tons/day of methanol from approximately 73 mmscfd of a sulfur-free natural gas process feedstock.

This application essentially consists of partial oxidation of the natural gas feedstock by reaction with air and steam so as to produce a nitrogen diluted synthesis gas, followed by passage of this synthesis gas through two synthesis reaction systems in series. The first synthesis system converts 50% of the carbon monoxide in the synthesis gas feed present into 100% pure cetane over an appropriate catalyst, according to the reaction:

and the second synthesis system converts 90% of the remaining CO into 100% pure methanol over an appropriate catalyst according to the reaction:

The residual combustible content of the gas leaving the seconds synthesis system is oxidized with air over an appropriate catalyst and the gas is then expanded to near atmospheric pressure in a turbine.

Figure 2:
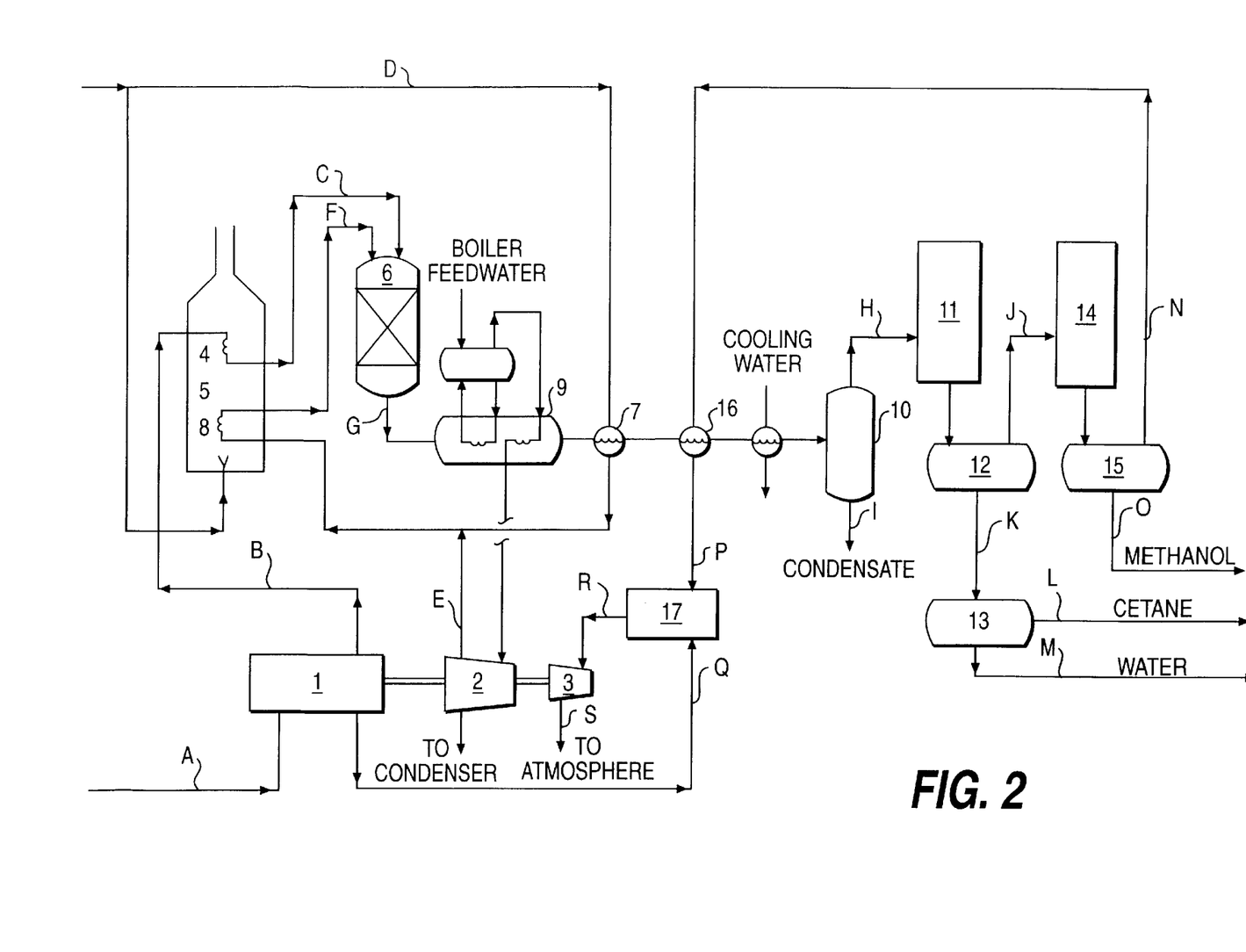
FIG. 2 is a flow diagram of a specific example of the present invention.

This description may be followed on the flowsheet identified as FIG. 2. The attached tables show the material flows, pressures and temperatures at the principal stages of the processing scheme.

An air compressor 1, driven by extraction/condensing steam turbine 2 and gas expansion turbine 3, ingests 32,298 lb mol/hr of air (dry basis) at point A. 26,651 lb mol/hr of this air is discharged from the compressor at 580 psig/320° F. at point B. The air is then heated in coil 4 in preheater furnace 5 to 930° F. at point C and passes at that temperature to catalytic partial oxidation reaction 6.

7966 lb mol/hr of sulfur-free natural gas enters the plant at point D at 600 psig/100° F. This gas is heated first in a heat exchanger 7 located in the product gas from reactor 6 to 750° F. The gas is then mixed with 96,276 lb/hr of steam which is extracted at point E from turbine 2 at 580 psig/750° F. It is then heated in coil 8 located in furnace 5 to 110° F. at Point F and passes at that temperature to reactor 6.

The air, natural gas and steam react in reactor 6 to produce 51,116 lb mol/hr of synthesis gas at 555 psig/200° F. at point G. This product gas is then cooled by indirect heat exchange in heat recovery boiler/superheater 9, then in exchangers 7 and 16, and in the subsequent cooler shown. The stream then enters separator 10, in which condensed excess process steam is removed. The process gas with a flow of 44,311 lb mol/hr leaves 10 at point H and the process condensate with a flow of 121,680 lb/hr leaves at point I, both at 480 psig/75° F.

The cooled synthesis gas stream next enters the first, cetane-producing synthesis system, represented by reactor 11, by which is to be understood an appropriate catalytic reactor system with the necessary heat exchangers and auxiliary equipment. The outlet stream from reactor 11 enters separator 12, in which a dry cetane-free gas stream is notionally separated from the cetane and water produced in reactor 11. The gas leaves this separator with a flow of 33758 lb mol/hr at point J and the cetane/water stream with a flow of 3706 lb mol/hr at point K, both at 450 psig/75° F. The cetane/water stream then flows to separator 13 in which the contents are separated into a cetane flow of 215.4 lb mol/hr, equivalent to 585 short tons/day, and a water flow of 62,838 lb/hr at point M. Both these streams leave the plant at 400 psig/750° F.

The gas stream at point J next enters the methanol-producing synthesis system, represented by reactor 14, by which is to be understood an appropriate catalytic reactor system with the necessary heat exchangers and auxiliary equipment. The outlet stream from reactor 14 enters separator 15, in which a methanol-free gas stream and a liquid methanol product are notionally completely separated. The gas leaves this separator at point N with a flow of 24,458 lb mol/hr and the liquid methanol product leaves at point P with a flow of 3100 lb mol/hr, equivalent to 1190 short tons/day.

The gas stream at point N is next heated in exchanger 16 by indirect heat exchange with the product gas from reactor 6, leaving 16 at point P at 400 psig/500° F. It then enters catalytic combustor 17, where it is joined by a flow of 5647 lb mol/hr (dry basis) of air at point Q from the discharge of compressor 1. The preheated air and gas streams leave 17 at point R at 395 psig/1500° F. with a flow of 29,226 lb mol/hr, with the combustible material present at point P completely oxidized. The hot gas then enters expansion turbine 3, leaving to atmosphere at point S at 560° F.

In a further embodiment, Block 201 of FIG. 1 represents a synthesis gas production unit wherein a feedstock 202, which may be a hydrocarbon gas or liquid or a carbonaneous solid such as coal or coke or a mixture of any of these substances, is reacted with a stream of oxygen-containing gas 203 containing at least about 30 molar percent of nitrogen, optional steam 204, optional carbon dioxide 205 and a gas rich in hydrocarbons 206 recycled from down-

| POINT DESCRIPTION | A AIR TO AIR COMP | B AIR TO PROCESS | C AIR TO PROCESS | D PROCESS FEEDSTOCK | E PROCESS STEAM | F FEEDSTOCK + STEAM | G RAW SYNGAS | H COOLED SYNGAS | I PROCESS CONDENSATE | J 1ST SYNTHESIS OFF-GAS |
|---|---|---|---|---|---|---|---|---|---|---|
| lb mol/hr | | | | | | | | | | |
| $H_2$ | — | — | — | — | — | — | 14,749 | 14,749 | — | 7,642 |
| CO | — | — | — | — | — | — | 6,891 | 6,891 | — | 3,445 |
| $CO_2$ | — | — | — | 37 | — | 37 | 1,479 | 1,479 | — | 1,479 |
| $N_2$ | 25,231 | 20,820 | 20,820 | 78 | — | 78 | 20,898 | 20,898 | — | 20,898 |
| $CH_4$ | — | — | — | 7,401 | — | 7,401 | 46 | 46 | — | 46 |
| $O_2$ | 6,766 | 5,583 | 5,583 | — | — | — | — | — | — | — |
| Ar | 301 | 248 | 248 | — | — | — | 248 | 248 | — | 248 |
| $C_2H_6$ | — | — | — | 382 | — | 382 | — | — | — | — |
| $C_3H_8$ | — | — | — | 58 | — | 58 | — | — | — | — |
| $C_4H_{10}$ | — | — | — | 10 | — | 10 | — | — | — | — |
| $C_{16}H_{34}$ | — | — | — | — | — | — | — | — | — | — |
| $CH_3OH$ | — | — | — | — | — | — | — | — | — | — |
| Total Dry | 32,298 | 26,651 | 26,651 | 7,966 | — | 7,966 | 44,311 | 44,311 | — | 33,758 |
| $H_2O$ | 1,303 | 69 | 69 | — | 5,344 | 5,344 | 6,805 | 45 | 6760 | — |
| Total Wet | 33,601 | 26,720 | 26,720 | 7,966 | 5,344 | 13,310 | 51,116 | 44,356 | 6760 | 33,750 |
| lb/hr | 958,474 | 772,778 | 772,778 | 136,842 | 96,192 | 233,031 | 1,005,812 | 884,132 | 121,680 | 772,620 |
| psig | 0 | 580 | 565 | 600 | 580 | 565 | 555 | 480 | 480 | 450 |
| °F. | 100 | 320 | 930 | 100 | 754 | 1100 | 2000 | 75 | 75 | 75 |

| POINT DESCRIPTION | K 1ST SYNTHESIS PRODUCT | L CETANE PRODUCT | M WATER BY-PRODUCT | N 2ND SYNTHESIS OFF-GAS | O METHANOL PRODUCT | P COMBUSTOR FEED GAS | Q COMBUSTION AIR | R COMBUSTION PRODUCT | S EXPANDED EXHAUST |
|---|---|---|---|---|---|---|---|---|---|
| lb mol/hr | | | | | | | | | |
| $H_2$ | — | — | — | 1,442 | — | 1,442 | — | — | — |
| CO | — | — | — | 345 | — | 345 | — | — | — |
| $CO_2$ | — | — | — | 1,479 | — | 1,479 | — | 1,870 | 1,870 |
| $N_2$ | — | — | — | 20,898 | — | 20,898 | 4,411 | 25,309 | 25,309 |
| $CH_4$ | — | — | — | 46 | — | 46 | — | — | — |
| $O_2$ | — | — | — | — | — | — | 1,183 | 197 | 197 |
| Ar | — | — | — | 248 | — | 248 | 53 | 301 | 301 |
| $C_2H_6$ | — | — | — | — | — | — | — | — | — |
| $C_3H_8$ | — | — | — | — | — | — | — | — | — |
| $C_4H_{10}$ | — | — | — | — | — | — | — | — | — |
| $C_{16}H_{34}$ | 215.4 | 215.4 | — | — | — | — | — | — | — |
| $CH_3OH$ | — | — | — | — | 3,100 | — | — | — | — |
| Total Dry | 215.4 | 215.4 | — | 24,458 | 3,100 | 24,458 | 5,647 | 27,677 | 27,677 |
| $H_2O$ | 3,491 | — | 3491 | — | — | — | 15 | 1,549 | 1,549 |
| Total Wet | 3,706 | 215.4 | 3491 | 24,458 | 3,100 | 24,548 | 5,662 | 29,226 | 29,226 |
| lb/hr | 111,512 | 48,680 | 62,838 | 673,420 | 99,200 | 673,420 | 163,754 | 837,174 | 837,174 |
| psig | 450 | 400 | 400 | 400 | 420 | 400 | 400 | 395 | — |
| °F. | 75 | 75 | 75 | 75 | 75 | 500 | 320 | 1,500 | 560 |

Figure 3:
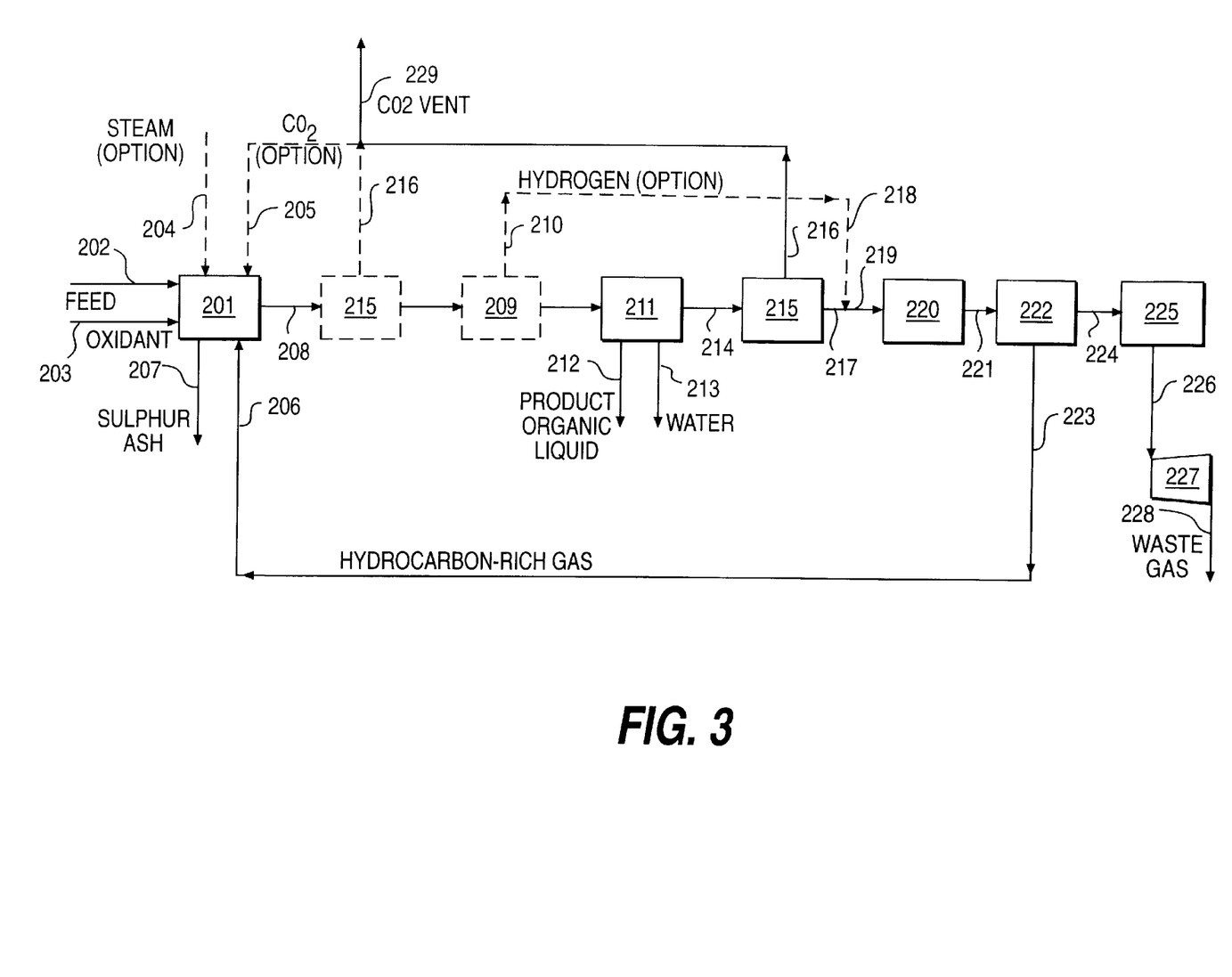
FIG. 3 comprises a flow diagram representing, inter alia, a synthesis gas production unit, a synthesis unit for the production of compounds which are liquids at atmospheric pressure as set forth in zone 5 of FIG. 1, a carbon dioxide removal unit, a hydrogen bypass and means for heating a nitrogen rich waste gas either by indirect heat transfer or by direct combustion with a oxidant to give a hot gas which is expanded in an expansion turbine or where such combustion is conducted in a combustion turbine to produce mechanical power before discharge to the atmosphere.

One of the advantages and distinguishing features of the present invention over the Garwood reference is the presence of a higher ratio of nitrogen to carbon monoxide and hydrogen in the vapor phase leaving the first reactor as compared to the ratio of these components in the feed gas. This results in a concomitant reduction of the partial pressure of water vapor at that point in the reaction due to the amount of nitrogen, which significantly improves the conversion of hydrogen and carbon monoxide into liquid hydrocarbons in the second reactor (and for that matter, in subsequent reactors if employed according to the invention). This is unexpected and not disclosed by Garwood.

stream as described below. Rejection of sulphur, ash and other waste materials is shown at 207. The product synthesis gas 208 contains hydrogen and carbon monoxide in a molar ratio up to about 4, but more typically about 2, plus the nitrogen content of stream 203. The pressure of the synthesis gas can be up to about 200 bar but usually ranges from about 10 bar to about 40 bar.

Block 209 represents an optional step for producing a hydrogen-rich gas stream 210 from the synthesis gas 208, for use downstream as described below. This stream preferably contains at least about 80 molar percent of hydrogen. Typical arrangements of 209 include a physical separation device such as a membrane or pressure swing adsorbers. This facility for by-passing hydrogen around the synthesis unit 211 could be used if passing any additional hydrogen needed for the downstream methanation through the synthesis unit is disadvantageous for the operation of the synthesis unit.

Block 211 represents a synthesis unit for the production of compounds 213 which are liquids at atmospheric pressure and temperature and are composed of carbon, hydrogen and optionally oxygen from the synthesis gas 208. The arrangement of the synthesis reactors within block 211 comprises a series of once-through reactors without recycle and with intermediate removal of product and corresponds with zone 5 of FIG. 1. Any water formed in the synthesis processes is discharged at 213. The tail gas 214 from the synthesis contains unreacted hydrogen and carbon monoxide, carbon dioxide, methane and a high proportion of nitrogen as its main constituents.

Block 215 represents a carbon dioxide removal process, using a solvent such as an amine solution or potassium carbonate solution. The $CO_2$ removed 216 may be recycled in part or wholly to form stream 205. Block 215 may optionally be located upstream of 211.

The scrubbed gas 217 is then optionally mixed with hydrogen rich gas 218 which may be derived from stream 210 and the combined gas stream 219 is then methanated in reactor(s) 220 to achieve essentially complete elimination of carbon oxides by reaction with the hydrogen present. The methanation again comprises reacting carbon monoxide and carbon dioxide in the gas stream with hydrogen to produce methane. The quantity of carbon dioxide removed in 215 and any amount of hydrogen added at 218 are adjusted to give an excess of hydrogen and especially a small excess of hydrogen in the methanator outlet gas 221 where the excess of hydrogen is measured by and not to exceed the quantity of hydrogen which has been consumed by methanation. The small excess would be from about 5% to about 25% of this hydrogen so consumed.

Stream 221 is then subjected to a physical separation process 222 which is typically a cryogenic process although an adsorptive or diffusional process may be substituted. The products from 222 are principally a hydrocarbon-rich gas stream 223, which is recycled to form stream 206, and a nitrogen-rich waste gas 224.

Stream 224 is typically heated 225 by indirect heat transfer or by direct combustion with an oxidant to give a hot gas 226 which is then expanded in an expansion turbine 227 to produce mechanical power before it is discharged to the atmosphere 228. Stream 221 can also be heated by such direct combustion in turbine 227 which may be a combustion turbine.

Figure 4:
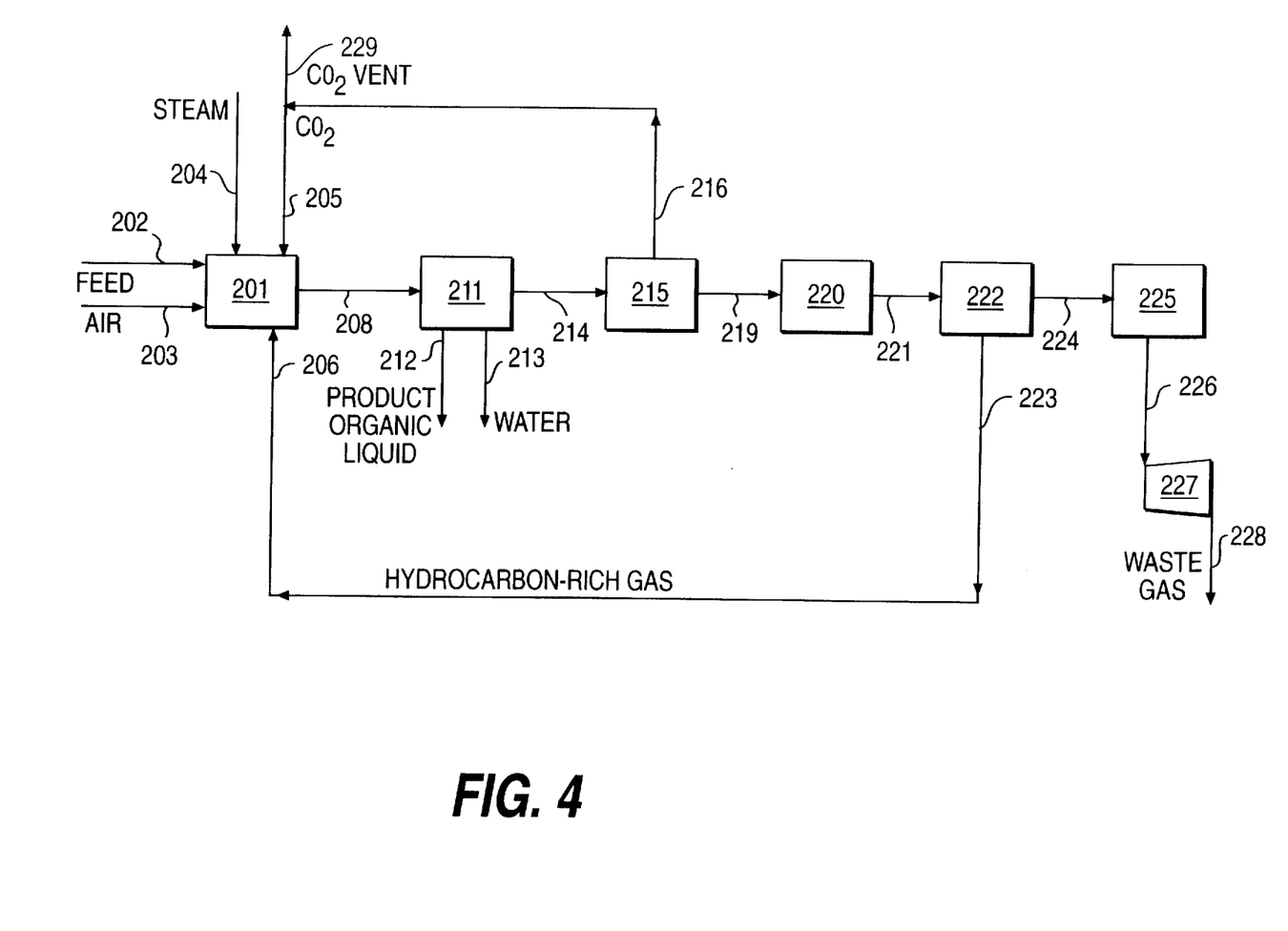
FIG. 4 is a flow diagram illustrating the production of octane from methane which, inter alia, does not include a hydrogen bypass.

The following material balance illustrates the production of octane from methane. Because all the hydrogen needed for the methanation stage passes in this example through the synthesis reactors 211, there is no hydrogen by-pass 210, 216 or unit 209. The resulting simplified flow scheme is shown in FIG. 4.

The example is based on 1000 kg mol/h of gross methane feed to the synthesis gas production unit (total in streams 202 and 206=895.2+104.8 kg mol/h).

Other parameters include:

Steam/carbon ratio for synthesis gas production=1.5

Outlet temperature from synthesis gas reactor=950° C.

Conversion of ($H_2$+CO) to octane=90%

$CO_2$ concentration in stream 219=0.5% molar

Methane concentration in streams 26, 223=50%

Hydrogen concentration in stream 224=2%.

The process conditions are shown in Table 1.

TABLE 1

| Stream No Description | 202* Natural Gas | 203* Oxidant (Air) | 204* Steam | 205* Recycled $CO_2$ | 206/223* Hydrocarbon- Rich Gas | 208* Synthesis Gas | 212* Octane Product |
|---|---|---|---|---|---|---|---|
| Flow (kg mol/h) | | | | | | | |
| $H_2$ | — | — | — | — | — | 1938.9 | — |
| CO | — | — | — | — | — | 826.9 | — |
| $CO_2$ | — | — | — | 266.7 | — | 431.9 | — |
| $N_2$ | — | 2242.2 | — | — | 104.8 | 2347.0 | — |
| $CH_4$ | 895.2 | — | — | — | 104.8 | 7.9 | — |
| $O_2$ | — | 601.3 | — | — | — | — | — |
| Ar | — | 26.7 | — | — | — | 26.7 | — |
| $C_8H_{18}$ | — | — | — | — | — | — | 93.0 |
| $H_2O$ | — | — | 1500.0 | — | — | — | — |
| Total | 895.2 | 2870.2 | 1500.0 | 266.7 | 209.6 | 5579.3 | 93.0 |

| Stream No Description | 213 Process Condensate | 214* Synthesis Tail Gas | 216* $CO_2$ Removed | 219* Methanator Feed | 221* Methanator Product | 224 Waste Gas | 229* $CO_2$ Vent |
|---|---|---|---|---|---|---|---|
| Flow (kg mol/h) | | | | | | | |
| $H_2$ | — | 357.5 | — | 357.5 | 52.6 | 52.6 | — |
| CO | — | 82.7 | — | 82.7 | — | — | — |
| $CO_2$ | — | 431.9 | 417.7 | 14.2 | — | — | 151.0 |
| $N_2$ | — | 2347.0 | — | 2347.0 | 2347.0 | 2242.2 | — |
| $CH_4$ | — | 7.9 | — | 7.9 | 104.8 | — | — |
| Ar | — | 26.7 | — | 26.7 | 26.7 | 26.7 | — |
| $H_2O$ | 744.2 | — | — | — | — | — | — |
| Total | 744.2 | 3253.7 | 417.7 | 2836.0 | 2531.1 | 2321.5 | 151.0— |

*Dry gas basis

In summary, the present invention in part is directed to a process for manufacturing an organic liquid comprising forming a gas comprising hydrogen, nitrogen and carbon monoxide by the partial oxidation of a hydrocarbon or other carbonaceous material with air. This gas is then passed, without the removal of the nitrogen, through two or more organic liquid synthesis reactors arranged in series, where the organic liquid synthesis reactors operate at a temperature ranging from about 200° F. to 500° F. and a pressure ranging from atmospheric pressure to about 100 atmospheres in the presence of a catalyst to form the organic liquid. The catalyst is selected from copper, iron or zinc compounds as the principal active constituents. The organic liquid is then condensed and removed from each of the reactors. The condensation process takes place at a temperature ranging from −200° to about 300° F. and a pressure ranging from atmospheric pressure to about 100 atmospheres.

In the foregoing process, a nitrogen rich waste gas is obtained from the step of condensing and removing the organic liquid from each of the reactors and the nitrogen rich waste gas is heated by indirect heat transfer or by direct combustion with an oxidant to produce a hot gas. The hot gas is then expanded in a turbine to produce mechanical power after which the hot gas is discharged to the atmosphere.

This process is specifically applicable to the manufacturer of organic liquids such as alcohols, olefins, and Fischer Tropsch products.

The process also includes manufacturing an organic liquid by a first step of forming a gas comprising hydrogen, nitrogen and carbon monoxide by the partial oxidation of a hydrocarbon or other carbonaceous material with air. This gas is passed, without the removal of the nitrogen, through two or more organic liquid synthesis reactors arranged in series. Organic liquid is condensed and removed from each of the reactors to obtain an organic liquid and a first product gas. Carbon dioxide is separated from the first product gas to obtain a second product gas or from the gas of the first step.

The next step comprises methanating the second product gas to obtain a third product gas which is substantially a hydrocarbon-rich gas stream. Again, methanation comprises reacting carbon monoxide and carbon dioxide in the gas stream with hydrogen to produce methane. The hydrocarbons are separated from the third product gas to obtain a nitrogen-rich waste gas followed by recycling the hydrocarbon-rich gas to the aforesaid first step for forming a gas comprising hydrogen, nitrogen and carbon monoxide. The nitrogen-rich waste gas is then heated by indirect heat transfer or by direct combustion to obtain a hot gas. The hot gas is expanded in a turbine to produce mechanical power before the hot gas is discharged to the atmosphere.

The immediately foregoing process further includes partially removing hydrogen from the gas formed in the first step and combining it with the second product gas obtained prior to (1) methanation of the second product gas, or (2) the separation of carbon dioxide from the first product gas, or from the first step along with the hydrogen added to the second product gas which is adjusted to give an excess of hydrogen in the third product gas obtained.

The immediately foregoing process can be further improved whereby the separation of carbon dioxide and the addition of hydrogen is adjusted to give a small excess of hydrogen in the third product gas. Furthermore, the carbon dioxide separated from the first product gas or from the gas of the first step is introduced into the first step for forming gas comprising hydrogen, nitrogen and carbon monoxide.

Lastly, steam may be introduced into the first step for forming a gas comprising hydrogen, nitrogen and carbon monoxide.

Other embodiments within the scope of this invention can be included and this invention is not limited to any particular embodiment but is only limited by the attached claims.

What is claimed is:

1. A process for manufacturing an organic liquid comprising:
   (a) forming a gas comprising hydrogen, nitrogen and carbon monoxide by the partial oxidation of a hydrocarbon or other carbonaceous material with air;
   (b) passing said gas without the removal or recycling of said nitrogen through two or more organic liquid synthesis reactors arranged in series, where said organic liquid synthesis reactors operate at a temperature ranging from about 200° F. to about 500° F. and a pressure ranging from atmospheric pressure to about 100 atmospheres in the presence of a catalyst selected from the group consisting of copper, iron, or zinc compounds as the principle active constituents to form said organic liquid; and
   (c) condensing and removing said organic liquid from each of said reactors, where said condensation process takes place at a temperature ranging from −200° F. to about 300° F. and a pressure ranging from atmospheric pressure to about 100 atmospheres.

2. The process according to claim 1, where two to about four organic liquid synthesis reactors are present.

3. The process according to claim 1, where waste gas from said organic liquid synthesis reactors is expanded to low pressure for use as a fuel.

4. The process according to claim 1, where waste gas from said organic liquid synthesis reactor is treated to recover the hydrogen or carbon monoxide content for recycle to an earlier stage in the process.

5. A process for manufacturing organic liquids wherein said liquids are alcohols, olefins and Fischer Tropsch products comprising:
   (a) forming a gas comprising hydrogen, nitrogen, and carbon monoxide by the partial oxidation of a hydrocarbon or other carbonaceous material with air;
   (b) passing said gas without the removal or recycling of said nitrogen through two or more organic liquid synthesis reactors arranged in series, where said organic liquid synthesis reactors operate at a temperature ranging from about 200° F. to about 500° F. and a pressure ranging from atmospheric pressure to about 100 atmospheres in the presence of a catalyst suitable for converting said gas to said organic liquid to form said organic liquid; and
   (c) condensing and removing said organic liquid from each of said reactors, where said condensation process takes place at a temperature ranging from −200° F. to about 300° F. and a pressure ranging from atmospheric pressure to about 100 atmospheres.

6. The process of claim 1 wherein a nitrogen rich waste gas is obtained from step (c) which is heated by indirect heat transfer or by direct combustion with an oxidant to produce a hot gas, said hot gas then being expanded in a turbine to produce mechanical power after which said hot gas is discharged to the atmosphere.

7. The process of claim 5 wherein a nitrogen rich waste gas is obtained from step (c) which is heated by indirect heat transfer or by direct combustion with an oxidant to produce a hot gas, said hot gas then being expanded in a turbine to produce mechanical power after which said hot gas is discharged to the atmosphere.

8. A process for manufacturing an organic liquid comprising:
   (a) forming a gas comprising hydrogen, nitrogen, carbon monoxide and carbon dioxide by the partial oxidation of a hydrocarbon or other carbonaceous material with air;
   (b) passing said gas without the removal or recycling of said nitrogen through two or more organic liquid synthesis reactors arranged in series to form said organic liquid;
   (c) condensing and removing said organic liquid from each of said reactors to obtain said organic liquid and a first product gas containing carbon dioxide
   (d) separating carbon dioxide from said first product gas to obtain a second product gas;
   (e) methanating any carbon dioxide or carbon monoxide that remains in said second product gas with said hydrogen to obtain a third product gas which is substantially a hydrocarbon-rich gas stream;
   (f) separating the hydrocarbons from said third product gas to obtain a nitrogen-rich waste gas and recycling said hydrocarbon rich gas to said step (a) for forming a gas comprising hydrogen, nitrogen, carbon monoxide and carbon dioxide.

9. The process of claim 8 wherein hydrogen formed in step (a) is partially removed from said gas and combined with said second product gas obtained from step (d) prior to methanation of said second product gas, the separation of carbon dioxide from said first product gas or from step (a) along with said hydrogen added to said second product gas obtained in step (d) being adjusted to give an excess of hydrogen in said third product gas obtained in step (e).

10. The process of claim 9 wherein said separation of carbon dioxide and said addition of hydrogen is adjusted to give a small excess of hydrogen in said third product gas.

11. The process of claim 8 wherein said carbon dioxide separated from said first product gas in step (d) or from said gas of step (a) is introduced into said step (a) for forming a gas comprising hydrogen, nitrogen and carbon monoxide.

12. The process of claim 10 wherein steam is introduced into said step (a) for forming a gas comprising hydrogen, nitrogen and carbon monoxide.

13. The process of claim 8 further comprising:
   (g) heating said nitrogen-rich waste gas by indirect heat transfer or by direct combustion with an oxidant to produce a hot gas; and
   (h) expanding said hot gas in a turbine to produce mechanical power before said hot gas is discharged to the atmosphere.

* * * * *

UNITED STATES PATENT AND TRADEMARK OFFICE
CERTIFICATE OF CORRECTION

PATENT NO. : 5,770,630
DATED : June 23, 1998
INVENTOR(S) : Wieslaw Mark KOWAL, et al It is certified that error appears in the above-identified patent and that said Letters Patent is hereby corrected as shown below:

ABSTRACT; Title Page, Penultimate line.

Change "se ies" to --series--.

MANUFACTURING OF ORGANIC LIQUIDS

Col. 1, line 14 change "new paragraph" to --and optionally hydrogen--;

line 19, change "reactio" to --reaction--;

line 28, change "locarbon" to --carbon--;

Col. 2, line 11, change "$H_2$- to --17 $H_2$--;

Col. 3, line 17, change "syn,thesis" to --synthesis--;

line 22, change "en-sure" to --ensure--;

line 23, change "diox-ide" to --dioxide--.

UNITED STATES PATENT AND TRADEMARK OFFICE
CERTIFICATE OF CORRECTION

PATENT NO. : 5,770,630
DATED : June 23, 1998
INVENTOR(S) : Wieslaw Mark KOWAL, et al It is certified that error appears in the above-identified patent and that said Letters Patent is hereby corrected as shown below:

Col. 3, line 30 Delete "preferred";

line 52, Change "inventionrelates" to --invention relates--;

IN THE CLAIMS

Claim 1, col. 12, line 28, change "100" to --100--.

Signed and Sealed this

Sixteenth Day of February, 1999

Attest:

Attesting Officer

*Acting Commissioner of Patents and Trademarks*